US012623984B2

(12) United States Patent
Takahashi

(10) Patent No.: US 12,623,984 B2
(45) Date of Patent: May 12, 2026

(54) AZEOTROPIC OR AZEOTROPE-LIKE COMPOSITION CONTAINING TRIFLUOROETHYLENE

(71) Applicant: DAIKIN INDUSTRIES, LTD., Osaka (JP)

(72) Inventor: Kazuhiro Takahashi, Osaka (JP)

(73) Assignee: DAIKIN INDUSTRIES, LTD., Osaka (JP)

(*) Notice: Subject to any disclaimer, the term of this patent is extended or adjusted under 35 U.S.C. 154(b) by 676 days.

(21) Appl. No.: 17/486,202

(22) Filed: Sep. 27, 2021

(65) Prior Publication Data

US 2022/0009861 A1     Jan. 13, 2022

Related U.S. Application Data

(63) Continuation of application No. PCT/JP2020/014230, filed on Mar. 27, 2020.

(30) Foreign Application Priority Data

Mar. 28, 2019    (JP) ................................. 2019-064670

(51) Int. Cl.
  *C07C 21/18*        (2006.01)
  *C09K 5/04*         (2006.01)
(52) U.S. Cl.
  CPC .............. *C07C 21/18* (2013.01); *C09K 5/045* (2013.01)
(58) Field of Classification Search
  CPC ................................. C07C 21/18; C09K 5/045
  See application file for complete search history.

(56) References Cited

U.S. PATENT DOCUMENTS

| | | | |
|---|---|---|---|
| 4,898,645 A | 2/1990 | Voigt et al. | |
| 2003/0098228 A1 | 5/2003 | Yoshii et al. | |
| 2014/0070132 A1 | 3/2014 | Fukushima | |
| 2015/0376486 A1 | 12/2015 | Hashimoto et al. | |
| 2016/0002518 A1 | 1/2016 | Taniguchi et al. | |
| 2016/0347693 A1* | 12/2016 | Fukushima | C07C 17/269 |

(Continued)

FOREIGN PATENT DOCUMENTS

| | | |
|---|---|---|
| EP | 2254851 | 10/2016 |
| JP | 2015-145452 | 8/2015 |

(Continued)

OTHER PUBLICATIONS

International Search Report (ISR) issued Jun. 30, 2020 in International (PCT) Application No. PCT/JP2020/014230.

(Continued)

*Primary Examiner* — Angela C Brown-Pettigrew
*Assistant Examiner* — Jiajia Janie Cai
(74) *Attorney, Agent, or Firm* — Wenderoth, Lind & Ponack, L.L.P.

(57)            ABSTRACT

Provided are a novel azeotropic or azeotrope-like composition, and a separation method using the composition. An object is to provide a novel azeotropic or azeotrope-like composition, and a separation method using the composition. A solution to achieve the object is to provide an azeotropic or azeotrope-like composition containing trifluoroethylene and at least one compound selected from the group consisting of 1,1-difluoroethylene, fluoroethylene, and trifluoromethane.

4 Claims, 1 Drawing Sheet

S15

S13

S11

C1

C2

S12

S14

(56)           References Cited

U.S. PATENT DOCUMENTS

| | | |
|---|---|---|
| 2018/0155259 A1 | 6/2018 | Ohkubo |
| 2019/0031934 A1 | 1/2019 | Fukushima et al. |

FOREIGN PATENT DOCUMENTS

| | | |
|---|---|---|
| JP | 2016-130236 | 7/2016 |
| JP | 2016-222603 | 12/2016 |
| WO | 2009/010472 | 1/2009 |
| WO | 2012/000853 | 1/2012 |
| WO | 2012/157764 | 11/2012 |
| WO | 2014/178352 | 11/2014 |
| WO | 2014/178353 | 11/2014 |

OTHER PUBLICATIONS

Kutub Uddin et al., "Low GWP Refrigerants for Energy Conservation and Environmental Sustainability", Advances in Solar Energy Research, Chapter 15, 2019, pp. 485-517.
Extended European Search Report issued Nov. 24, 2022 in corresponding European Patent Application No. 20777363.1.
English language translation of International Preliminary Report on Patentability issued Sep. 28, 2021 in corresponding International (PCT) Patent Application No. PCT/JP2020/014230.
"Azeotropic Data-III", compiled by Lee H. Horsley, Advances in Chemistry, American Chemical Society, pp. 63, 93, 96, 100, XP9530941, 1973.
Ikuhoi Yamada et al., "On the Study of Azeotropic Pressure, Temperature and Composition of Azeotrope of Binary System", Journal of the Japan Petroleum Institute, vol. 3, No. 1, pp. 25-29, XP55745054, 1960.

* cited by examiner

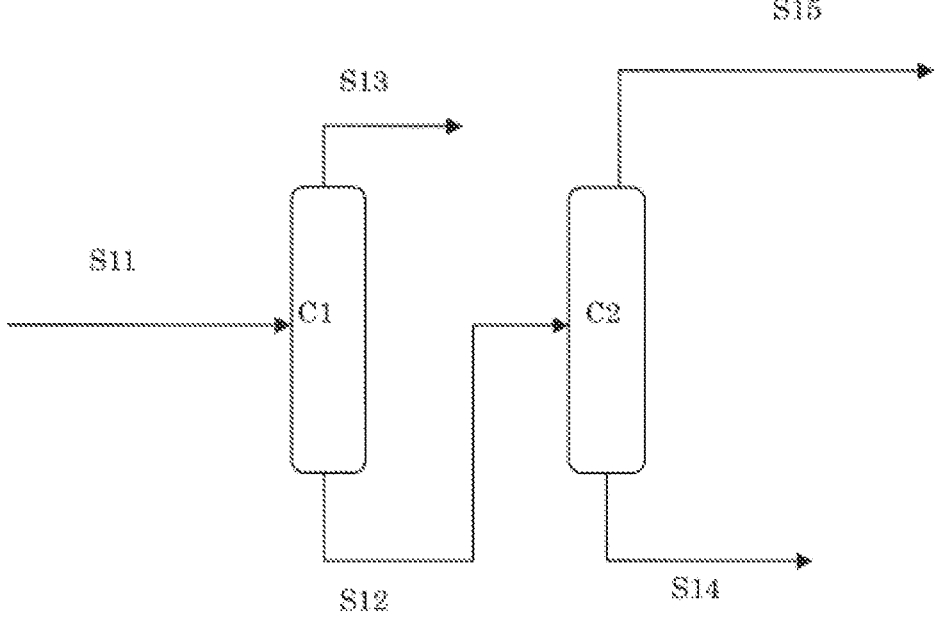

AZEOTROPIC OR AZEOTROPE-LIKE COMPOSITION CONTAINING TRIFLUOROETHYLENE

TECHNICAL FIELD

The present disclosure relates to an azeotropic or azeotrope-like composition containing trifluoroethylene ("HFO-1123" below).

BACKGROUND ART

A refrigerant is proposed that contains trifluoroethylene ($CHF=CF_2$) as HFO (hydrofluoroolefin), which is HFC of an olefin with low global warming potential (PTL 1).

Trifluoroethylene can be produced by, for example, subjecting 1,1,1,2-tetrafluoroethane to an HF elimination reaction in the presence of a catalyst (PTL 2). Trifluoroethylene can also be produced by reducing 1-chloro-2,2,2-trifluoroethylene with hydrogen (PTL 3).

CITATION LIST

Patent Literature

PTL 1: WO2012/157764A
PTL 2: WO2009/010472A
PTL 3: WO2012/000853A

SUMMARY

Item 1.

An azeotropic or azeotrope-like composition comprising trifluoroethylene (HFO-1123) and at least one compound selected from the group consisting of 1,1-difluoroethylene (HFO-1132a), fluoroethylene (HFO-1141), and trifluoromethane (HFC-23).

Advantageous Effects

The present disclosure provides a novel azeotropic or azeotrope-like composition, and a separation method using the azeotropic or azeotrope-like composition.

BRIEF DESCRIPTION OF DRAWINGS

FIG. 1 shows an example of the process of separation by distillation using an azeotropic or azeotrope-like composition.

DESCRIPTION OF EMBODIMENTS

Definition of Terms

In the present specification, the term "refrigerant" includes at least compounds that are specified in ISO 817 (International Organization for Standardization), and that are given a refrigerant number (ASHRAE number) representing the type of refrigerant with "R" at the beginning; and further includes refrigerants that have properties equivalent to those of such refrigerants, even though a refrigerant number is not yet given. Refrigerants are broadly divided into fluorocarbon compounds and non-fluorocarbon compounds, in terms of the structure of the compounds. Fluorocarbon compounds include chlorofluorocarbons (CFC), hydrochlorofluorocarbons (HCFC), and hydrofluorocarbons (HFC). Non-fluorocarbon compounds include propane (R290), propylene (R1270), butane (R600), isobutane (R600a), carbon dioxide (R744), ammonia (R717), and the like.

In the present specification, the phrase "composition comprising a refrigerant" at least includes (1) a refrigerant itself (including a mixture of refrigerants); (2) a composition that further comprises other components, and that can be mixed with at least a refrigeration oil to obtain a working fluid for a refrigerating machine; and (3) a working fluid for a refrigerating machine containing a refrigeration oil. In the present specification, of these three embodiments, the composition (2) is referred to as a "refrigerant composition" so as to distinguish it from a refrigerant itself (including a mixture of refrigerants). Further, the working fluid for a refrigerating machine (3) is referred to as a "refrigeration oil-containing working fluid" so as to distinguish it from the "refrigerant composition."

In the present specification, the term "azeotrope-like composition" refers to a composition that can be handled in substantially the same manner as azeotropic compositions. Specifically, in the present specification, the term "azeotrope-like composition" means a mixture composed of two or more substances that behave substantially as a single substance with a constant boiling point, or substantially a constant boiling point. A feature of an azeotrope-like composition is that vapor generated by evaporating or distilling the composition in liquid form has a formulation substantially unchanged from the formulation of the liquid. Specifically, in the present specification, a mixture that can be boiled, distilled, or refluxed without a substantial compositional change is referred to as an "azeotrope-like composition." Specifically, a composition having a difference between the bubble-point pressure and the dew-point pressure of 3 percent or less (based on the bubble-point pressure) at a specific temperature is defined as an azeotrope-like composition in the present disclosure.

In the present specification, when the term "alternative" is used in a context in which the first refrigerant is replaced with the second refrigerant, the first type of "alternative" means that equipment designed for operation using the first refrigerant can be operated using the second refrigerant under optimum conditions, optionally with changes of only a few parts (at least one of the following: refrigeration oil, gasket, packing, expansion valve, dryer, and other parts) and equipment adjustment. In other words, this type of alternative means that the same equipment is operated with an alternative refrigerant. Embodiments of this type of "alternative" include "drop-in alternative," "nearly drop-in alternative," and "retrofit," in the order in which the extent of changes and adjustment necessary for replacing the first refrigerant with the second refrigerant is smaller.

The term "alternative" also includes a second type of "alternative," which means that equipment designed for operation using the second refrigerant is operated for the same use as the existing use with the first refrigerant by using the second refrigerant. This type of alternative means that the same use is achieved with an alternative refrigerant.

In the present specification, the term "refrigerating machine" refers to machines in general that draw heat from an object or space to make its temperature lower than the temperature of ambient air, and maintain a low temperature. In other words, refrigerating machines refer to conversion machines that gain energy from the outside to do work, and that perform energy conversion, in order to transfer heat from where the temperature is lower to where the temperature is higher.

In the present specification, pressure refers to absolute pressure, unless otherwise indicated.

The present inventor found that trifluoroethylene obtained by conventional production methods contains at least one compound selected from the group consisting of 1,1-difluoroethylene, fluoroethylene, and trifluoromethane, and a composition containing these compounds forms an azeotrope-like composition that can be handled as if it were a single component. The inventor then completed the present disclosure.

1. Azeotropic or Azeotrope-Like Composition

The azeotropic or azeotrope-like composition according to the present disclosure is an azeotropic or azeotrope-like composition that contains trifluoroethylene and at least one compound selected from the group consisting of 1,1-difluoroethylene, fluoroethylene, and trifluoromethane.

The azeotropic or azeotrope-like composition according to the present disclosure contains trifluoroethylene in an amount of preferably 50 mass % or more, more preferably 60 mass % or more, and still more preferably 70 mass or more, based on the entire composition, from the standpoint of separation efficiency and yield in the purification step, handling of the composition as a heat transfer medium, and performance.

The azeotropic or azeotrope-like composition according to the present disclosure contains trifluoroethylene and at least one compound selected from the group consisting of 1,1-difluoroethylene, fluoroethylene, and trifluoromethane in a total amount of preferably 60 mass, or more, more preferably 80 mass % or more, and still more preferably 90 mass or more, based on the entire composition. The azeotropic or azeotrope-like composition according to the present disclosure may be composed only of trifluoroethylene and at least one compound selected from the group consisting of 1,1-difluoroethylene, fluoroethylene, and trifluoromethane.

The azeotropic or azeotrope-like composition according to the present disclosure may be an azeotropic or azeotrope-like composition containing
- (a) trifluoroethylene,
- (b) at least one compound selected from the group consisting of 1,1-difluoroethylene, fluoroethylene, and trifluoromethane, and
- (c) at least one additional compound selected from the group consisting of fluoroethane, 1,1,2-trifluoroethane, 2-chloro-1,1,1-trifluoroethane, 1-chloro-1,1,2-trifluoroethane, 2,2-dichloro-1,1,1-trifluoroethane, 1,1-difluoroethane, 1,2-difluoroethane, and 1,1,1,2-tetrafluoroethane.

When containing components (a), (b), and (c) above, the azeotropic or azeotrope-like composition according to the present disclosure contains the additional compound (c) in an amount of preferably 0.1 mass % or more and less than 30 mass %, more preferably 0.1 mass % or more and less than 10 mass %, and still more preferably 0.1 mass %, or more and less than 1 mass %, based on the entire composition, from the standpoint of handling of the composition as a heat transfer medium and performance.

When containing components (a), (b), and (c) above, the azeotropic or azeotrope-like composition according to the present disclosure contains components (a), (b), and (c) in an total amount of preferably 60 mass or more, more preferably 80 mass % or more, and still more preferably 90 mass % or more, based on the entire composition, from the standpoint of handling of the composition as a heat transfer medium and performance. The azeotropic or azeotrope-like composition according to the present disclosure may be composed only of components (a), (b), and (c) above.

The azeotropic or azeotrope-like composition according to the present disclosure has a GWP of preferably 750 or less, more preferably 150 or less, and still more preferably 10 or less.

The azeotropic or azeotrope-like composition according to the present disclosure is preferably used as a refrigerant, a heat transfer medium, a foaming agent, or a propellant. These compositions have a low global warming potential, and are comparable in performance to conventionally used HFC refrigerants; for example, refrigerants such as R-410A, R-407C, and R-404A. These compositions can also prevent global warming with their low GWP.

2. Heat Transfer Medium Composition

When used as a heat transfer medium composition, the azeotropic or azeotrope-like composition according to the present disclosure is also usable as a refrigerant with a lower global warming potential (GWP) that replaces a conventionally used HFC refrigerant such as HFC134a, R-410A, R-407C, or R-404A; or a component of a refrigerant.

The azeotropic or azeotrope-like composition according to the present disclosure used as a heat transfer medium composition may further comprise at least one other component. The azeotropic or azeotrope-like composition according to the present disclosure can be further mixed with at least a refrigeration oil to obtain a working fluid for a refrigerating machine (the composition according to the present disclosure in this case being referred to as "the refrigerant composition according to the present disclosure").

The refrigerant composition according to the present disclosure may comprise at least one of the following other components, if necessary. The other components are not limited; specific examples include water, tracers, ultraviolet fluorescent dyes, stabilizers, and polymerization inhibitors.

When the refrigerant composition according to the present disclosure is used as a working fluid in a refrigerating machine, it is generally used as a mixture with at least a refrigeration oil. Thus, it is preferable that the refrigerant composition according to the present disclosure does not substantially contain a refrigeration oil. Specifically, in the refrigerant composition according to the present disclosure, the content of the refrigeration oil based on the entire refrigerant composition is preferably 0 to 1 mass %, and more preferably 0 to 0.1 mass %.

The refrigerant composition according to the present disclosure may contain a small amount of water. The water content of the refrigerant composition is preferably 0.1 mass % or less, based on the entire refrigerant. A small amount of water contained in the refrigerant composition stabilizes double bonds in the molecules of unsaturated fluorocarbon compounds that can be present in the refrigerant, and makes it less likely that the unsaturated fluorocarbon compounds will be oxidized, thus increasing the stability of the refrigerant composition.

A tracer is added to the refrigerant composition according to the present disclosure at a detectable concentration such that when the refrigerant composition has been diluted, contaminated, or undergone other changes, the tracer can trace the changes.

The refrigerant composition according to the present disclosure may comprise a single tracer, or two or more tracers.

The tracer is not limited, and can be suitably selected from commonly used tracers.

Examples of tracers include hydrofluorocarbons, hydrochlorofluorocarbons, chlorofluorocarbons, hydrochlorocarbons, fluorocarbons, deuterated hydrocarbons, deuterated hydrofluorocarbons, perfluorocarbons, fluoroethers, brominated compounds, iodinated compounds, alcohols, aldehydes, ketones, and nitrous oxide ($N_2O$). The tracer is particularly preferably a hydrofluorocarbon, a hydrochlorofluorocarbon, a chlorofluorocarbon, a hydrochlorocarbon, a fluorocarbon, or a fluoroether.

The following compounds are preferable as a tracer.

FC-14 (tetrafluoromethane, $CF_4$)

HCC-40 (chloromethane, $CH_3Cl$)

HFC-23 (trifluoromethane, $CHF_3$)

HFC-41 (fluoromethane, $CH_3Cl$)

HFC-125 (pentafluoroethane, $CF_3CHF_2$)

HFC-134a (1,1,1,2-tetrafluoroethane, $CF_3CH_2F$)

HFC-134 (1,1,2,2-tetrafluoroethane, $CHF_2CHF_2$)

HFC-143a (1,1,1-trifluoroethane, $CF_3CH_3$)

HFC-152 (1,2-difluoroethane, $CH_2FCH_2F$)

HFC-245fa (1,1,1,3,3-pentafluoropropane, $CF_3CH_2CHF_2$)

HFC-236fa (1,1,1,3,3,3-hexafluoropropane, $CF_3CH_2CF_3$)

HFC-236ea (1,1,1,2,3,3-hexafluoropropane, $CF_3CHFCHF_2$)

HFC-227ea (1,1,1,2,3,3,3-heptafluoropropane, $CF_3CHFCF_3$)

HCFC-22 (chlorodifluoromethane, $CHClF_2$)

HCFC-31 (chlorofluoromethane, $CH_2ClF$)

CFC-1113 (chlorotrifluoroethylene, $CF_2{=}CClF$)

HFE-125 (trifluoromethyl-difluoromethyl ether, $CF_3OCHF_2$)

HFE-134a (trifluoromethyl-fluoromethyl ether, $CF_3OCH_2F$)

HFE-143a (trifluoromethyl-methyl ether, $CF_3OCH_3$)

HFE-227ea (trifluoromethyl-tetrafluoroethyl ether, $CF_3OCHFCF_3$)

HFE-236fa (trifluoromethyl-trifluoroethyl ether, $CF_3OCH_2CF_3$)

The refrigerant composition according to the present disclosure may comprise a tracer in a total amount of about 10 parts per million by weight (ppm) to about 1000 ppm, based on the entire refrigerant composition. The refrigerant composition according to the present disclosure may comprise a tracer in a total amount of preferably about 30 ppm to about 500 ppm, and more preferably about 50 ppm to about 300 ppm, based on the entire refrigerant composition.

The refrigerant composition according to the present disclosure may comprise a single ultraviolet fluorescent dye, or two or more ultraviolet fluorescent dyes.

The ultraviolet fluorescent dye is not limited, and can be suitably selected from commonly used ultraviolet fluorescent dyes.

Examples of ultraviolet fluorescent dyes include naphthalimide, coumarin, anthracene, phenanthrene, xanthene, thioxanthene, naphthoxanthene, fluorescein, and derivatives thereof. The ultraviolet fluorescent dye is particularly preferably either naphthalimide or coumarin, or both.

The refrigerant composition according to the present disclosure may comprise a single stabilizer, or two or more stabilizers.

The stabilizer is not limited, and can be suitably selected from commonly used stabilizers.

Examples of stabilizers include nitro compounds, ethers, and amines.

Examples of nitro compounds include aliphatic nitro compounds, such as nitromethane and nitroethane; and aromatic nitro compounds, such as nitrobenzene and nitrostyrene.

Examples of ethers include 1,4-dioxane.

Examples of amines include 2,2,3,3,3-pentafluoropropylamine and diphenylamine.

Examples of stabilizers also include butylhydroxyxylene and benzotriazole.

The content of the stabilizer is not limited. Generally, the content of the stabilizer is preferably 0.01 to 5 mass %, and more preferably 0.05 to 2 mass %, based on the entire refrigerant.

The refrigerant composition according to the present disclosure may comprise a single polymerization inhibitor, or two or more polymerization inhibitors.

The polymerization inhibitor is not limited, and can be suitably selected from commonly used polymerization inhibitors.

Examples of polymerization inhibitors include 4-methoxy-1-naphthol, hydroquinone, hydroquinone methyl ether, dimethyl-t-butylphenol, 2,6-di-tert-butyl-p-cresol, and benzotriazole.

The content of the polymerization inhibitor is not limited. Generally, the content of the polymerization inhibitor is preferably 0.01 to 5 mass %, and more preferably 0.05 to 2 mass %, based on the entire refrigerant.

The composition according to the present disclosure can also be used as a refrigeration oil-containing working fluid for a refrigerating machine (this composition being referred to as "the refrigeration oil-containing working fluid according to the present disclosure"). The refrigeration oil-containing working fluid according to the present disclosure comprises at least the refrigerant composition according to the present disclosure and a refrigeration oil, and is used as a working fluid in a refrigerating machine. Specifically, the refrigeration oil-containing working fluid according to the present disclosure is obtained by mixing a refrigeration oil used in a compressor of a refrigerating machine with a refrigerant or refrigerant composition. The refrigeration oil-containing working fluid generally comprises 10 to 50 mass % of refrigeration oil.

The refrigeration oil-containing working fluid according to the present disclosure may comprise a single refrigeration oil, or two or more refrigeration oils.

The refrigeration oil is not limited, and can be suitably selected from commonly used refrigeration oils. In this case, refrigeration oils that are superior in the action of increasing the miscibility with the mixture and the stability of the mixture, for example, are suitably selected as necessary.

The base oil of the refrigeration oil is preferably, for example, at least one member selected from the group consisting of polyalkylene glycols (PAG), polyol esters (POE), and polyvinyl ethers (PVE).

The refrigeration oil may further comprise additives in addition to the base oil. The additive may be at least one member selected from the group consisting of antioxidants, extreme-pressure agents, acid scavengers, oxygen scavengers, copper deactivators, rust inhibitors, oil agents, and antifoaming agents.

A refrigeration oil with a kinematic viscosity of 5 to 400 cSt at 40° C. is preferable from the standpoint of lubrication.

The refrigeration oil-containing working fluid according to the present disclosure may further optionally comprise at least one additive. Examples of additives include the compatibilizing agents described below.

The refrigeration oil-containing working fluid according to the present disclosure may comprise a single compatibilizing agent, or two or more compatibilizing agents.

The compatibilizing agent is not limited, and can be suitably selected from commonly used compatibilizing agents.

Examples of compatibilizing agents include polyoxyalkylene glycol ethers, amides, nitriles, ketones, chlorocarbons, esters, lactones, aryl ethers, fluoroethers, and 1,1,1-trifluoroalkanes. The compatibilizing agent is particularly preferably a polyoxyalkylene glycol ether.

3. Separation Method

The azeotropic or azeotrope-like composition according to the present disclosure can serve as an important composition in performing azeotropic distillation for separating trifluoroethylene from a mixture of trifluoroethylene and at least one compound selected from the group consisting of 1,1-difluoroethylene, fluoroethylene, and trifluoromethane; or from a mixture of trifluoroethylene, above compound (b), and above additional compound (c).

For example, trifluoroethylene can be separated in some cases by extracting an azeotropic or azeotrope-like composition containing trifluoroethylene and at least one compound selected from the group consisting of 1,1-difluoroethylene, fluoroethylene, and trifluoromethane from a composition containing at least trifluoroethylene and at least one compound selected from the group consisting of 1,1-difluoroethylene, fluoroethylene, and trifluoromethane by performing azeotropic distillation.

Azeotropic distillation refers to a separation method in which the composition to be separated by a distillation column is one or more azeotropic mixtures or azeotropic-mixture-like compositions; the distillation column is operated under conditions for separating the composition to be separated; and the properties of the azeotropic and azeotrope-like composition are used in order to separate the composition.

Azeotropic distillation can occur when only the components of the mixture to be separated are distilled, or when a component that forms an azeotropic mixture with one or more components of the initial mixture is added. A method that works in this manner, i.e., a method that forms an azeotropic mixture with one or more components of the mixture desired to be separated, and that facilitates the separation of these components by distillation, is azeotropic distillation.

Embodiments are described above; however, it can be understood that various changes in forms and details can be made without departing from the spirit and scope of the claims.

Item 1.

An azeotropic or azeotrope-like composition comprising trifluoroethylene (HFO-1123) and at least one compound selected from the group consisting of 1,1-difluoroethylene (HFO-1132a), fluoroethylene (HFO-1141), and trifluoromethane (HFC-23).

Item 2.

The azeotropic or azeotrope-like composition according to Item 1, comprising the trifluoroethylene in an amount of 50 mass % or more based on the entire azeotropic or azeotrope-like composition.

Item 3.

The azeotropic or azeotrope-like composition according to Item 1 or 2, further comprising at least one additional compound selected from the group consisting of fluoroethane, 1,1,2-trifluoroethane, 2-chloro-1,1,1-trifluoroethane, 1-chloro-1,1,2-trifluoroethane, 2,2-dichloro-1,1,1-trifluoroethane, 1,1-difluoroethane, 1,2-difluoroethane, and 1,1,1,2-tetrafluoroethane.

Item 4.

The azeotropic or azeotrope-like composition according to Item 3, comprising the additional compound in an amount of 0.1 mass % or more and less than 30 mass % based on the entire azeotropic or azeotrope-like composition.

Item 5.

The azeotropic or azeotrope-like composition according to any one of Items 1 to 4, which is for use as a heat transfer medium.

EXAMPLES

Example 1

Table 1 shows vapor-liquid equilibrium data (20° C.) of 1,1-difluoroethylene (HFO-1132a)/HFO-1123.

TABLE 1

| Liquid Phase HFO-1132a (mole frac) | Gas Phase HFO-1132a (mole frac) | Total pressure MPa |
|---|---|---|
| 0.01 | 0.016 | 1.84 |
| 0.05 | 0.076 | 1.90 |
| 0.10 | 0.147 | 1.98 |
| 0.20 | 0.276 | 2.14 |
| 0.30 | 0.392 | 2.31 |
| 0.40 | 0.496 | 2.48 |
| 0.50 | 0.592 | 2.65 |
| 0.60 | 0.681 | 2.83 |
| 0.70 | 0.764 | 3.02 |
| 0.80 | 0.844 | 3.21 |
| 0.85 | 0.883 | 3.31 |
| 0.9 | 0.922 | 3.41 |
| 0.99 | 0.922 | 3.61 |
| 0.999 | 0.999 | 3.63 |

In this system, no azeotropic composition is present. However, an azeotrope-like composition forms within the range of HFO-1132a/HFO-1123=0.1/99.9 (mol %) to 15/85 and HFO-1132a/HFO-1123=85/15 (mol %) to 99.9/0.1.

Table 2 shows vapor-liquid equilibrium data (40° C.) of fluoroethylene (HCFO-1141)/HFO-1123.

TABLE 2

| Liquid Phase HFO-1141 (mol frac) | Gas Phase HFO-1141 (mole frac) | Total pressure MPa |
|---|---|---|
| 0.001 | 0.0013 | 3.51 |
| 0.01 | 0.013 | 3.52 |
| 0.05 | 0.065 | 3.56 |
| 0.10 | 0.127 | 3.62 |
| 0.20 | 0.240 | 3.71 |
| 0.30 | 0.342 | 3.79 |
| 0.40 | 0.438 | 3.85 |
| 0.50 | 0.528 | 3.90 |
| 0.60 | 0.616 | 3.93 |
| 0.70 | 0.704 | 3.95 |
| 0.75 | 0.750 | 3.95 |
| 0.80 | 0.795 | 3.95 |
| 0.90 | 0.892 | 3.92 |
| 0.95 | 0.944 | 3.90 |
| 0.99 | 0.988 | 3.88 |
| 0.999 | 0.999 | 3.88 |

Under the above conditions, the azeotropic formulation is HFO-1141/HFO-1123=75/25 (mol %) and 80/20 (mass %). An azeotrope-like composition forms within the range of HFO-1141/HFO-1123=0.1/99.9 (mol %) to 99.9/0.1.

Table 3 shows vapor-liquid equilibrium data (20° C.) of trifluoromethane (HFC-23)/HFO-1123.

TABLE 3

| Liquid Phase HFC-23 (mole frac) | Gas Phase HFC-23 (mole frac) | Total pressure MPa |
|---|---|---|
| 0.001 | 0.0017 | 1.83 |
| 0.05 | 0.08 | 1.96 |
| 0.10 | 0.15 | 2.04 |
| 0.15 | 0.23 | 2.12 |
| 0.20 | 0.29 | 2.22 |
| 0.30 | 0.41 | 2.41 |
| 0.40 | 0.52 | 2.61 |
| 0.50 | 0.62 | 2.81 |
| 0.60 | 0.71 | 3.04 |
| 0.70 | 0.79 | 3.28 |
| 0.80 | 0.86 | 3.54 |
| 0.85 | 0.89 | 3.76 |
| 0.90 | 0.93 | 3.84 |
| 0.95 | 0.97 | 4.00 |
| 0.99 | 0.99 | 4.17 |
| 0.999 | 0.999 | 4.20 |

In this system, no azeotropic composition is present. An azeotrope-like composition forms within the range of HFC-23/HFO-1123=0.1/99.9 (mol %) to 15/85 and HFC-23/HFO-1123=85/15 (mole) to 99.9/0.1.

Example 2: Process for Separating HFO-1123 and HFO-1141

FIG. 1 shows an example of the process of separation by distillation using an azeotropic composition. Table 4 shows the results. From S11, a composition containing HFO-1123 and HFO-1141 is fed to a distillation column C1. From S13, an azeotropic composition of HFO-1123 and HFO-1141 flows out, and a composition of HFO-1123 and HFO-1141 in which HFO-1123 is more concentrated compared with S11 is obtained. From S12, HFO-1123 in which the concentration of HFO-1141 is lowered is obtained. S12 is sent to the next step. In C2, components such as HFC-161 and HFC-152a are further concentrated and separated into S14. From S15, high-purity HFO-1123 is obtained. A combination of distillation operations as described here enables the recovery of high-purity HFO-1123.

TABLE 4

| | Flow Rate (kg/hr) | | | | |
|---|---|---|---|---|---|
| | S11 | S12 | S13 | S14 | S15 |
| HFO1123 | 9.80 | 8.91 | 0.89 | 0.12 | 8.79 |
| HFO1141 | 0.10 | 0.008 | 0.092 | 0.00 | 0.008 |
| HFO1132a | 0.02 | 0.00 | 0.02 | 0.00 | 0.00 |
| HFC161 | 0.02 | 0.02 | 0.00 | 0.02 | 0.00 |
| HFC152a | 0.01 | 0.01 | 0.00 | 0.01 | 0.00 |
| HFC152 | 0.02 | 0.02 | 0.00 | 0.02 | 0.00 |
| HFC143 | 0.02 | 0.02 | 0.00 | 0.02 | 0.00 |
| HFC134a | 0.01 | 0.01 | 0.00 | 0.01 | 0.00 |

The operation pressure for the distillation columns was adjusted as described below.

Operation pressure of distillation column C1: 1.5 MPaG, column top temperature: 13° C., column bottom temperature: 14° C.

Operation pressure of distillation column C2: 1.4 MPaG, column top temperature: 12° C., column bottom temperature: 28° C.

Example 3

The refrigerating capacity of each composition was determined by simulation. The COP and refrigerating capacity are indicated by the ratio relative to R-410A. Table 5 shows the results. The calculation conditions for the refrigeration cycle are as follows. Peng-Robinson was used as the physical properties model.

Evaporation temperature: 10° C., condensation temperature: 45° C., degree of superheat: 5° C., degree of supercooling: 5° C., compression efficiency: 70%

TABLE 5

| Components | Formulation | GWP | COP (relative to 410A) | Refrigerating Capacity (relative to 410A) |
|---|---|---|---|---|
| HFO-1123/HFO-1132a | 99/1 | 1 | 0.891 | 1.069 |
| HFO-1123/HFO-1132a | 85/15 | 1 | 0.860 | 1.103 |
| HFO-1123/HFO-1141 | 99/1 | 1 | 0.896 | 1.071 |
| HFO-1123/HFO-1141 | 90/10 | 1 | 0.904 | 1.118 |
| HFO-1123/HFO-1141 | 80/20 | 1 | 0.914 | 1.166 |
| HFO-1123/HFC-23 | 99/1 | 125 | 0.891 | 1.071 |
| HFO-1123/HFC-23 | 90/10 | 1241 | 0.858 | 1.119 |
| HFO-1123/HFC-23 | 80/20 | 2581 | 0.818 | 1.168 |

The invention claimed is:

1. An azeotropic or azeotrope-like composition consisting of (a) trifluoroethylene, (b) at least one compound selected from the group consisting of fluoroethylene and trifluoromethane, and (c) at least one additional compound selected from the group consisting of fluoroethane, 2-chloro-1,1,1-trifluoroethane, 2,2-dichloro-1,1,1-trifluoroethane, and 1,2-difluoroethane, wherein the additional compound (c) is contained in an amount of 0.1 mass % or more and less than 1 mass % based on the entire azeotropic or azeotrope-like composition.

2. The azeotropic or azeotrope-like composition according to claim 1, wherein the trifluoroethylene in present in an amount of 50 mass % or more based on the entire azeotropic or azeotrope-like composition.

3. The azeotropic or azeotrope-like composition according to claim 1, which is for use as a heat transfer medium.

4. The azeotropic or azeotrope-like composition according to claim 2, which is for use as a heat transfer medium.

* * * * *